US009927343B2

(12) United States Patent
Braumandl (10) Patent No.: US 9,927,343 B2
(45) Date of Patent: Mar. 27, 2018

(54) APPARATUS AND METHOD FOR DETERMINING A SIZE OF PARTICLES IN A SPRAY JET

(71) Applicant: Sensor Instruments Entwicklungs—und Vertriebs GmbH, Thurmansbang (DE)

(72) Inventor: Walter Braumandl, Thurmansbang (DE)

(73) Assignee: SENSOR INSTRUMENTS ENTWICKLUNGS—UND VERTRIEBS GMBH, Thurmansbang (DE)

( * ) Notice: Subject to any disclaimer, the term of this patent is extended or adjusted under 35 U.S.C. 154(b) by 118 days.

(21) Appl. No.: 15/178,831

(22) Filed: Jun. 10, 2016

(65) Prior Publication Data
US 2016/0363520 A1    Dec. 15, 2016

(30) Foreign Application Priority Data
Jun. 11, 2015   (DE) .................. 10 2015 007 506

(51) Int. Cl.
*G01N 15/02*   (2006.01)
*G01N 15/14*   (2006.01)
*G01N 15/00*   (2006.01)

(52) U.S. Cl.
CPC ..... *G01N 15/0205* (2013.01); *G01N 15/1434* (2013.01); *G01N 15/1459* (2013.01);
(Continued)

(58) Field of Classification Search
CPC .......... G01N 15/0205; G01N 15/1459; G01N 15/1434; G01N 2015/1486; G01N 2015/0046; G01N 2015/1493
(Continued)

(56) References Cited

U.S. PATENT DOCUMENTS 4,548,499 A   10/1985 Eisert et al.
4,701,051 A   10/1987 Buchhave et al.
(Continued)

FOREIGN PATENT DOCUMENTS

DE      4326979 C1    3/1995
DE      19845363 A1   4/2000
(Continued)

*Primary Examiner* — Hina F Ayub
*Assistant Examiner* — Amanda Merlino
(74) *Attorney, Agent, or Firm* — J-TEK LAW PLLC; Jeffrey D. Tekanic; Scott T. Wakeman (57) ABSTRACT

An apparatus for detecting a size of particles in a spray jet includes a substantially square frame. A first emitter unit and a first detection unit, and a second emitter unit and a second detection unit, are respectively provided at opposite corners of the frame. Two light beams that cross each other in a focus are generated by the respective emitter units. Passage of a particle through the focus is detected based on light intensity signals from the first and second detection units. Using another set of light beams that cross each other and that are separated from the above-noted light beams in the direction of flight of the particle, passage of the particle through a second common focus can be detected. Particle velocity and particle size can be obtained based on the time difference between the passage of the particle through the two foci.

20 Claims, 5 Drawing Sheets

(52) U.S. Cl.
CPC ............... *G01N 2015/0046* (2013.01); *G01N 2015/1486* (2013.01); *G01N 2015/1493* (2013.01)

(58) Field of Classification Search
USPC ................................................ 356/335–343
See application file for complete search history.

(56) References Cited

U.S. PATENT DOCUMENTS

| | | | |
|---|---|---|---|
| 4,986,659 A | | 1/1991 | Bachalo |
| 5,502,561 A | * | 3/1996 | Hutchins ............ G01N 15/0205 356/336 |
| 5,684,575 A | | 11/1997 | Steen |
| 2009/0210165 A1 | | 8/2009 | Christensen et al. |
| 2014/0268142 A1 | | 9/2014 | Tropea et al. |
| 2014/0268143 A1 | | 9/2014 | Tropea et al. |

FOREIGN PATENT DOCUMENTS

| | | |
|---|---|---|
| DE | 102012102361 A1 | 2/2013 |
| DE | 102012102363 A1 | 2/2013 |
| DE | 102012102364 A1 | 9/2013 |
| EP | 0144310 B1 | 8/1987 |
| EP | 0447529 B1 | 1/1997 |
| EP | 0638797 B1 | 11/1998 |
| EP | 0689672 B1 | 2/2000 |

* cited by examiner

APPARATUS AND METHOD FOR DETERMINING A SIZE OF PARTICLES IN A SPRAY JET

CROSS-REFERENCE

The present application claims priority to German patent application serial number 10 2015 007 506.3 filed on Jun. 11, 2015, the contents of which are incorporated fully herein by reference.

TECHNICAL FIELD

The present invention generally relates to an apparatus and a method for determining a size of particles in a spray jet, such as e.g., an apparatus and a method that makes possible in-line spray jet control, including a determination of particle size and particle velocity. Such spray jet control may be used, e.g., in the fields of die spraying, spray painting, spray drying or powder coating.

BACKGROUND ART

Methods are known in which a measurement has to be performed outside a running manufacturing process, because the techniques used do not allow for a real-time measurement.

However, DE 198 45 363 A1 discloses a laser measuring device for on-line measurement of particle size distributions in manufacturing processes. The measuring method is performed in accordance with the "time of transition" principle, wherein a laser beam is highly focused and scanned over the particles to be measured by a deflection unit. The laser radiation is collected behind the measurement plane and measured by a detector. If the deflected beam hits a particle, it is temporarily interrupted. The particle size can be calculated from the duration of this interruption and the known deflection velocity of the beam.

SUMMARY OF THE INVENTION

It is an object of the present teachings to disclose improved apparatuses and improved methods for determining a size of particles in a spray jet during a manufacturing process, i.e. in real-time. In preferred embodiments of the present teachings, both the velocity and the size of particles, as well as the number of particles per unit time, may be determined in real-time at any arbitrary location in the spray jet during a manufacturing process.

In one aspect of the present teachings, an apparatus for determining a size of particles in a spray jet may preferably include one or more first light sources (e.g., one or more laser diodes) emitting a first light beam and a second light beam, and one or more second light sources (e.g., one or more laser diodes) emitting a third light beam and a fourth light beam. A first focusing unit, e.g., including at least one first lens, focuses the first and second light beams in a first focus and a second focus, respectively. The first focus is spaced apart from the second focus by a distance in a first direction (z), which may be collinear or substantially collinear with the direction of movement of the particles in the spray jet. A second focusing unit, e.g., including at least one second lens, focuses the third and fourth light beams in the first focus and the second focus, respectively.

A first detection unit, e.g., including one or more photodetectors such as one or more photodiodes, detects an intensity of the first light beam and an intensity of the second light beam after the first and second light beams have passed through the first focus and the second focus, respectively. A second detection unit, e.g., including one or more photodetectors such as one or more photodiodes, detects an intensity of the third light beam and an intensity of the fourth light beam after the third and fourth light beams have passed through the first focus and the second focus, respectively. An evaluation unit, e.g., including a processor or microprocessor configured to execute a stored program, determines the size of a particle that has passed through the first focus and the second focus based, at least in part, on the intensities detected by the first detection unit and the second detection unit.

Additional objects, embodiments, features and advantages of the present teachings will become apparent from the following description of detailed embodiments and from the claims with reference to the figures.

DETAILED DESCRIPTION OF THE EMBODIMENTS

In certain aspects of the present teachings, an apparatus and a method are provided that make possible a spatial resolution of about 0.1 mm. In order to achieve this, two focused laser beams are used, which laser beams are, e.g., arranged orthogonal to each other in a plane perpendicular to the spray direction, preferably, to the central axis of the spray jet. Using an appropriate optical system, a laser emission area, e.g., an emission area of a laser diode, is imaged onto a detector with a scale of approximately 1:1. In order to achieve an angle of convergence of the laser light cone that is as large as possible, an optical system having a relatively large diameter is used. When both laser beams are precisely focused in a common focus or focus region, an intersection area is formed at the position where the two laser beams cross each other (intersect). The intersection area may have a diameter on the order of 0.01 mm. With this design, particles having a size of upwards of 0.001 mm can be detected in the common focus of the two laser beams.

The present teachings are based, in part, upon the concept that, when an individual particle passes through the common focus, the detected intensities of both laser beams decrease approximately at the same time. From this simultaneous decrease, it can be determined that the particle has passed exactly through the common focus. Thus, individual (single) particles can be specifically localized in the spray jet. By moving the common focus of the two laser beams along the direction of the spray jet, particle size can be determined at any arbitrary location in the spray jet.

In order to determine a velocity of a particle, each laser beam is mirrored or duplicated, e.g., by using a plane-parallel glass plate. In such an embodiment, two (virtual) planes arranged in succession along the flight direction (movement path) of the particles in the spray jet (i.e., the spray direction) can be defined, wherein the respective laser beams or foci lie in the two planes. The distance between the two planes is determined, e.g., by the thickness of the plane-parallel glass plate and the angle of the same to the optical axis of the laser. Whether a particle has first passed through the common focus of the two laser beams lying (propagating) in the first plane and then through the common focus of the two laser beams lying (propagating) in the second plane can be determined based on the detection signals or the temporal variation of the intensities. Based on the time interval between the resulting decreases in the detected intensities, the velocity of the particle in the direction perpendicular to the two planes can be determined. Based on this determined velocity, the particle size can then be determined from the duration of the decrease of the intensities of one or more of the laser beams, as will be further explained below.

Figure 1:
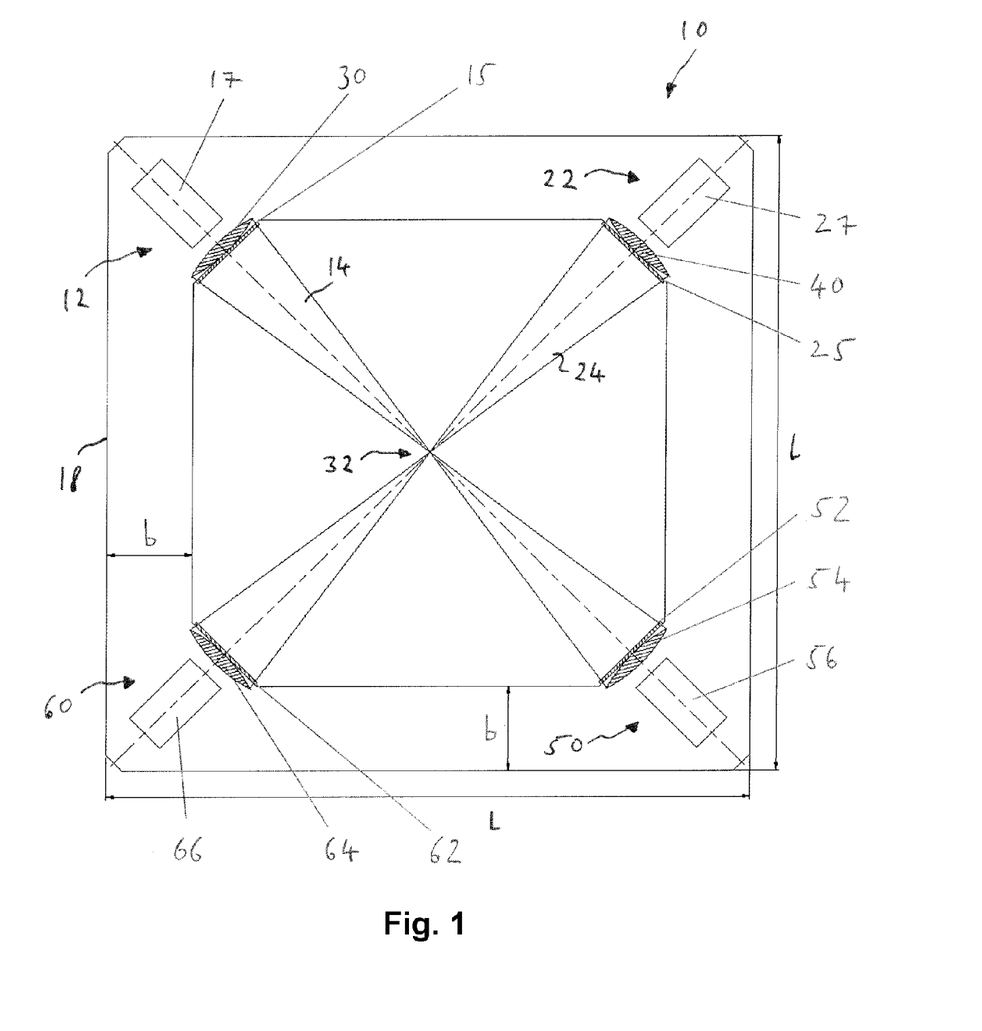
FIG. 1 is a schematic front view of an apparatus for determining a particle size in accordance with an exemplary embodiment.

Referring to FIG. 1, an exemplary embodiment of an apparatus 10 for determining a particle size in a spray jet is shown. The apparatus 10 includes a substantially rectangular or square frame 18 having a width b. An outer dimension L of frame 18 may, e.g., be 600 mm by 600 mm, and a thickness may, e.g., be 80 mm. The width b can be selected such that the inner diameter of the frame 18 is, e.g., about 400 mm by 400 mm. In any case, frame 18 is configured such that the spray jet including the particles to be detected may pass through the interior of the frame without affecting the associated manufacturing process.

Figure 2:
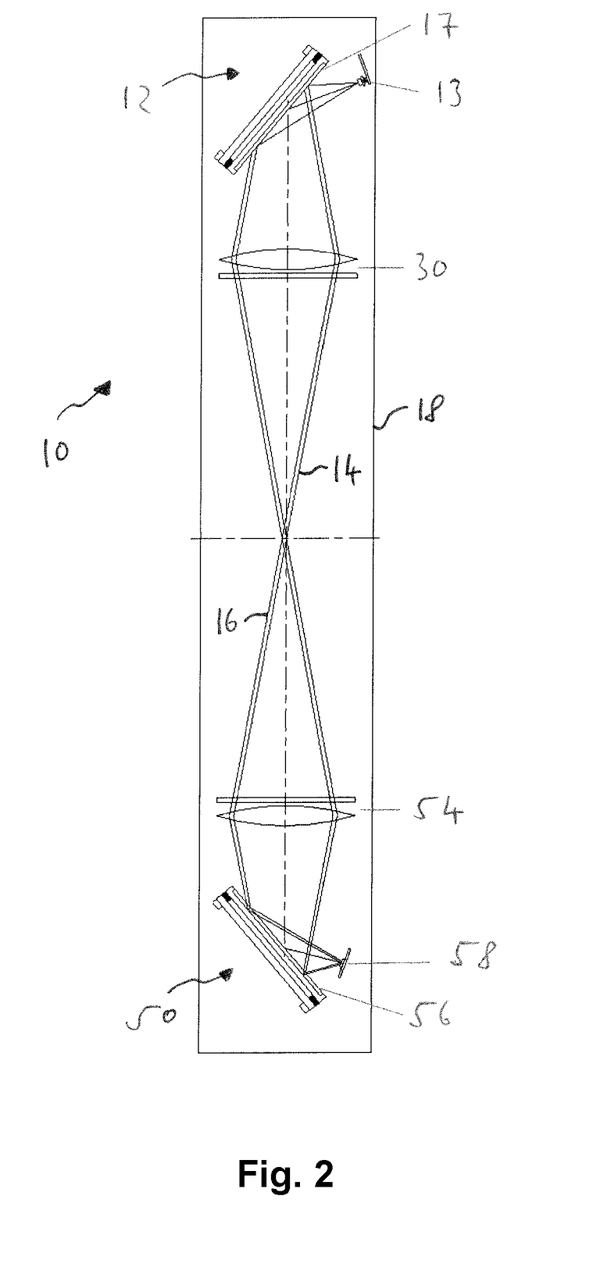
FIG. 2 is a schematic side view of the apparatus in accordance with the exemplary embodiment.
Figure 3:
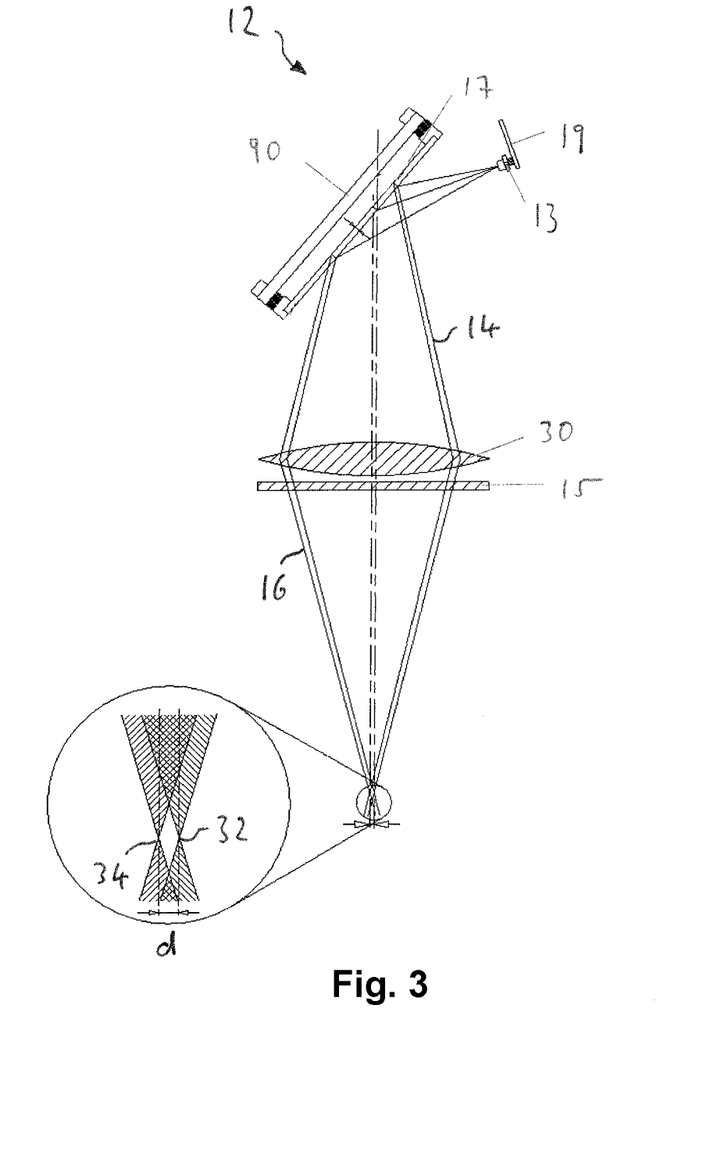
FIG. 3 is a schematic illustration of an emitter unit included in the apparatus in accordance with the exemplary embodiment.

As shown in FIG. 2, frame 18 is formed as a hollow frame. Within frame 18, as shown in FIG. 1, a first emitter unit 12 and a first detector unit 50, and a second emitter unit 22 and a second detector unit 60, are respectively arranged at opposite corners. As shown in FIGS. 1 and 2, first emitter unit 12 is configured to emit a first light beam 14 and a second light beam 16 in parallel in a first direction (z), which will be explained in more detail below. In a preferred embodiment, first emitter unit 12 may include a light source 13, e.g., a laser diode, and a plane-parallel plate 17, as shown in FIG. 3 in more detail, wherein the light beam emitted from light source 13 is directed onto plane-parallel plate 17, i.e. a structure having two plates disposed in parallel to each other. It should be noted that, if necessary, devices for moving light source 13 and plane-parallel plate 17 may be provided. For example, a mechanical adjustment unit 90 may be provided for adjusting the angle of plane-parallel plate 17 with respect to light source 13. Emission of the light beam by light source 13 may be controlled by a driver circuit 19 provided, e.g., on a circuit board on which light source 13 is mounted.

Figure 5:
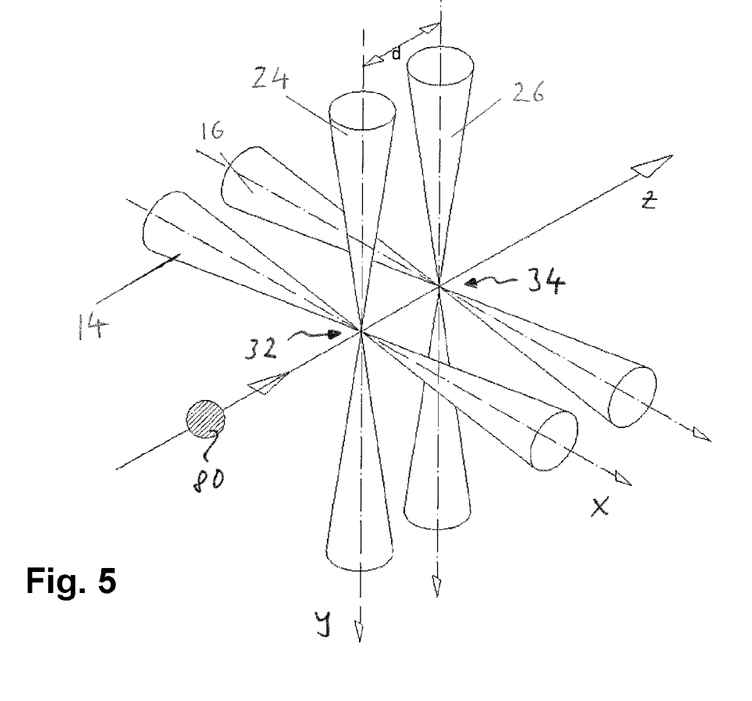
FIG. 5 shows the beam paths of the light beams that are used for determining the particle size in accordance with the exemplary embodiment.

As shown in FIG. 3, the light beam impinging on the plane-parallel plate, e.g., a glass plate, is reflected by the same. This results in a first reflection on the surface of plane-parallel plate 17, and second reflection occurs on the rear side of plane-parallel plate 17. This results in a second light beam 16 in addition to the first light beam 14, with the second light beam 16 being offset from the first light beam 14. In particular, as shown in FIG. 5, second light beam 16 is separated from first light beam 14 by a distance d in a direction z that substantially corresponds to the spray direction of the spray jet. In the present embodiment, the first light beam 14 extends in a first plane perpendicular to the spray direction z in a first direction x, while second light beam 16 extends in the first direction x in a second plane that is spaced from the first plane by the distance d. Therefore, the two light beams 14, 16 are parallel to each other. It will be readily appreciated that the planes in which the respective light beams 14, 16 propagate are defined by frame 18 and by the arrangement of emitter unit 12, in particular, plane-parallel plate 17, inside frame 18. Further, it will be appreciated that, in order to determine a particle size, the frame has to be positioned such that the direction of flight of the particles in the spray jet is substantially perpendicular to the plane that is defined by frame 18.

Returning to FIGS. 1 and 2, a first focusing unit 30, e.g., an appropriate lens such as a biconvex lens, is provided in front of first emitter unit 12. The first focusing unit 30 is configured to focus the first and second light beams 14, 16 in a first focus 32 and a second focus 34, respectively, which are shown in FIGS. 3 and 5. The first focusing unit 30 is arranged within frame 18, similar to the first emitter unit 12. An opening in frame 18 that is aligned with units 12, 30 is closed by a window 15 that is transparent for light beams 14, 16 such that the units are protected from the outside.

As shown in FIG. 1, a second emitter unit 22 is also provided in frame 18 at a corner of frame 18 that is adjacent to the first emitter unit. The second emitter unit 22 is configured in substantially the same manner as the first emitter unit 12, with a corresponding light source, a plane-parallel plate 27, an associated second focusing unit 40, which is configured identically to first focusing unit 30, and a window 25. Therefore, a detailed description of second emitter unit 22 and second focusing unit 40 is omitted.

As shown in FIG. 5, second emitter unit 22 is configured to emit a third light beam 24 and a fourth light beam 26 in parallel in a third direction y, the third direction y being perpendicular to the flight direction z of the particle 80 and also substantially perpendicular to the first direction x, which is the direction of propagation of first and second light beams 14, 16. Furthermore, third and fourth light beams 24, 26 are focused in first focus 32 and second focus 34, respectively, by second focusing unit 40, with first and second light beams 14, 16 also being focused therein. As such, two foci 32, 34 are defined in succession along the flight direction z of the particles 80. As shown in FIG. 1, each of foci 32 and 34 lies at the center of frame 18.

Figure 4:
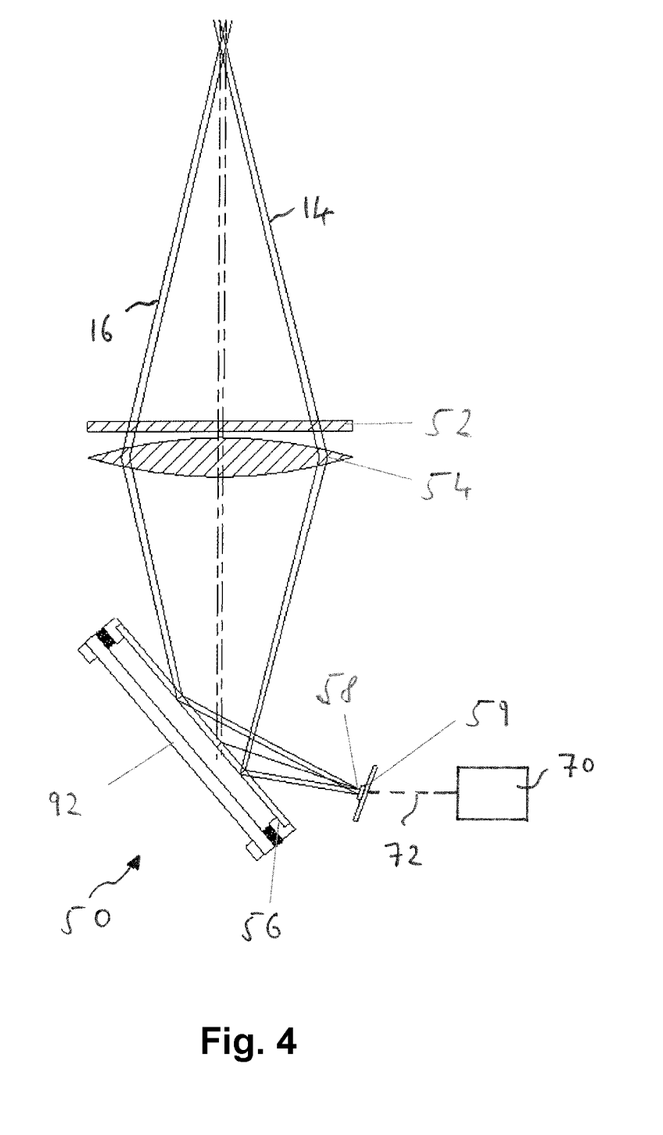
FIG. 4 is a schematic illustration of a detector unit included in the apparatus in accordance with the exemplary embodiment.

In order to detect the intensities of the light beams 14, 16, 24, 26 emitted from emitter units 12, 22, first detection unit 50 and second detection unit 60 are also provided in frame 18. First detection unit 50, which is shown in more detail in FIG. 4, is configured to detect an intensity E1 of first light beam 14 and an intensity E2 of second light beam 16 after passage of the light beams through the first focus 32 and the second focus 34, respectively. In other words, as shown in FIG. 1, first detection unit 50 is arranged at the corner of frame 18 that is opposite to first emitter unit 12, and second detection unit 60 is arranged at the corner of frame 18 that is opposite to second emitter unit 22. In the exemplary embodiment, first detection unit 50 includes a mirror 56 for beam deflection and a detection element 58, e.g., a differential photodiode. Detection element 58 is mounted on a circuit board on which an appropriate electronic circuit 59, e.g., for amplifying the output signal provided by detection element 58 may also be provided. Further, as shown in FIG. 4, detection element 58 is in communication with an evaluation unit 70, e.g., via electronic circuit 59 and a wired or wireless communication link 72. Evaluation unit 70 may therefore receive the output signal provided by detection element 58 and determine a detected intensity based thereon.

As also shown in FIG. 4, first detection unit 50 further includes a mechanical adjusting unit 92, which may adjust deflection mirror 56 with respect to detection element 58. Further, an optical system 54, e.g., a lens such as a biconvex lens, is associated with first detection unit 50. The optical system 54 directs light beams 14, 16 entering an interior portion of frame 18 via window 52 to deflection mirror 56 and focuses light beams 14, 16 onto detection element 58. By an appropriate adjustment (movement) of adjusting unit 92, the imaged light beams 14, 16 may be directed onto detection element 58 in such a manner that their intensities can be detected.

Second detection unit 60 is configured substantially identical to first detection unit 50. Therefore, a detailed description of second detection unit 60, in particular, a deflection mirror 66, an optical system or lens 64 and a window 62 is omitted. It should be understood that evaluation unit 70 is also in communication with the detection element (not shown) of second detection unit 60 via an appropriate communication link to receive an output signal that indicates the detected intensities of the third and fourth light beams 24, 26. Also, it should be noted that, although a single first detection unit 50 may be provided to detect the intensities of both of the first and second light beams 14, 16 and a single second detection unit 60 may be provided to detect the intensities of both of the third and fourth light beams 24, 26, the intensity of each light beam may be detected by an individual detector dedicated to detecting the intensity of only one light beam.

Figure 6:
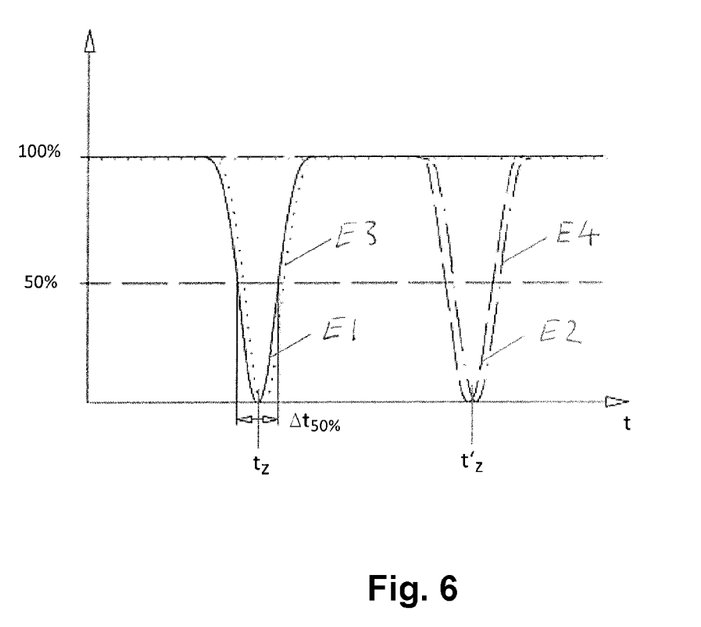
FIG. 6 shows a temporal variation of the intensities of the light beams in FIG. 5 detected upon passage of a particle through the light beams.

In the following, a method for determining a size of a particle 80 in the spray jet that is performed using the exemplary apparatus 10 will be described with reference to FIGS. 5 and 6.

As described above, evaluation unit 70 receives output signals from the detection elements of first detection unit 50 and second detection unit 60. When the first emitter unit 12 and the second emitter unit 22 emit the light beams 14, 16 and 24, 26, respectively, and no particle interrupts said light beams, a maximum intensity of the light beams is detected by the corresponding detection unit. This maximum intensity is indicated as 100% in FIG. 6.

When a particle 80 passes through one of the light beams, this light beam is interrupted or partially interrupted by the particle. Therefore, the detected intensity of the light beam is reduced. It is understood that the reduction will be greater when the particle is larger or when the particle interrupts the light beam closer to the focus of the light beam. As previously mentioned, apparatus 10 is configured such that the diameter of the focus is sufficiently small such that, when a particle having a typical size passes through the focus, the light beam is interrupted completely or substantially completely, whereby the intensity is reduced to approximately zero in this case.

Evaluation unit 70 is configured to determine the size and/or velocity of a particle 80 that has passed (moved) through first focus 32 and second focus 34 when frame 18 is arranged substantially perpendicular to the direction of the spray jet in or around said spray jet, based on the intensities detected by the first detection unit 50 and the second detection unit 60.

Preferably, evaluation unit 70 determines, based on a comparison of the intensities E1, E2 (and/or the temporal variation of the same) of the first and second light beams 14, 16 to each other and/or the intensities E3, E4 (and/or the temporal variation of the same) of the third and fourth light beams 24, 26 detected by second detection unit 60, whether a particle 80 has moved first through first focus 32 and then through second focus 34 along the flight direction z. In particular, it can be determined whether particle 80 has passed through first focus 32 based on a comparison of the intensities E1 and E3 of the first and third light beams 14, 24. This is because, in case particle 80 does not pass through first focus 32, the reduction of the intensities will be different for the intensities E1 and E3. For example, it is possible that particle 80 may pass through first light beam 14, such that the intensity of the same is reduced, however, a simultaneous reduction of the intensity E3 of third light beam 24 only occurs when particle 80 passes through the common first focus 32. While it may also be conceivable that, at the same time at which a first particle 80 passes through first light beam 14 outside of first focus 32, another particle passes through third light beam 24 outside of first focus 32, such that intensities E1 and E3 are reduced simultaneously or in a similar manner due to this coincidence, in this case, the amount of reduction would be smaller or would at least vary in a different manner as compared to the passage of a particle through the common first focus 32. Therefore, by determining whether a simultaneous reduction of intensities E1 and E3 occurs, which may, e.g., be below a predetermined threshold, it can be determined with sufficient certainty/probability that a particle 80 has passed through common first focus 32. As shown in FIG. 6, this may be the case at time $t_z$, e.g., when a simultaneous reduction of the intensities to approximately zero occurs.

The same determination can also be made with respect to the intensities E2 and E4 of light beams 16, 26. Therefore, as shown in FIG. 6, it can be determined that a particle has passed through common focus 34 at time $t'_z$. Further, it is necessary to determine in an appropriate manner whether it is the same particle 80 that has passed through first focus 32. This can be achieved, e.g., based on a comparison of the intensities E1 and E3 to the intensities E2 and E4 (and/or the temporal variation thereof). Alternatively or additionally, a time window can be defined that corresponds to a maximum and/or a minimum expected velocity of particle 80. In case the time difference between the times $t_z$ and $t'_z$ lies within this time window, it can be assumed with sufficient certainty that the same particle 80 has passed through both foci 32, 34 in the flight direction z. After this determination, the velocity of the particle 80 can be determined by evaluation unit 70. In particular, the velocity v is given by the previously mentioned distance d between the two foci divided by the time difference $t'_z$ minus $t_z$, i.e., $v=d/(t'_z-t_z)$.

Based on the determined velocity of particle 80, evaluation unit 70 may then determine the size of particle 80. This determination may be based on the velocity v and the duration of a reduction of the intensities of one or more of light beams 14, 16, 24, 26 as particle 80 passes through foci 32, 34. In principle, it would be sufficient to only use the temporal variation of one of the intensities E1, E2, E3, E4 and to define an appropriate criterion that indicates a period of time associated with the passage of the particle 80. For example, a full duration at half maximum $\Delta t_{50\%}$ could be used. The "full duration at half maximum" is the time period between when the detected intensity drops below 50% and when the detected intensity rises again above 50%. The size of particle 80 could then be determined by multiplying the determined velocity v by the period of time $\Delta t_{50\%}$. However, more accurate results can be obtained when the particle size is determined based on two or more of the intensities E1, E2, E3, E4 by averaging the respective values of $\Delta t_{50\%}$. Therefore, the size or diameter D of particle 80 can be determined, e.g., based on the following equation:

$$D = v \cdot (\Delta t_{50\% \; E1} + \Delta t_{50\% \; E2} + \Delta t_{50\% \; E3} + \Delta t_{50\% \; E4})/4$$

In some applications of the present teachings, the right-side of the above-noted equation optionally may be further multiplied by an empirically-determined proportional constant (k), if necessary. In addition or in the alternative, the velocity v of the particle may be determined by calculating the derivative of one or more portions (e.g., a portion of the upward slope and/or a portion the downward slope, e.g., at or encompassing the 50% intensity value) of one or more of the four intensity curves. In addition or in the alternative, one or more of the full duration at half maximum values may be omitted, e.g., if one or two of the values is significantly different from two close values.

Evaluation unit 70 may also be configured to generate corresponding statistics with respect to the velocity and the size of particles in the spray jet at the positions defined by frame 18 and foci 32, 34. Therefore, e.g., statistics can be obtained that indicate the number of particles per unit time passing through foci 32, 34 at a specific position within the spray jet. Further, a distribution of the sizes of the particles at this position in the spray jet could be obtained. Based on this distribution, an average particle size may be determined. Further, frame 18 could be manually or automatically moved while the measurements are being performed on the spray jet, e.g., by appropriate holders and positioning devices, such that a two-dimensional distribution of, e.g., the particle size and the particle velocity could be obtained, in accordance with the position in the spray jet. Numerous further quantities could be obtained by using an appropriate evaluation mechanism.

As previously mentioned, frame 18 of apparatus 10 may be brought into the spray jet during a manufacturing process, such that evaluation unit 70 may determine the size and velocity of the particles in the spray jet in real-time. Further, it is also conceivable that frame 18 can be automatically positioned or moved with respect to the spray jet by using a holder and/or an appropriate positioning device, e.g., to determine the above-mentioned distribution of the sizes and velocities of the particles in the spray jet.

In the exemplary embodiment described above, the first and second light beams 14, 16 are arranged at an angle of at least substantially 90° to the third and fourth light beams 24, 26. However, it should be understood that, in other embodiments, other non-zero angles could be used to determine whether a particle 80 has passed through the common focus of the light beams. Further, in the embodiment described above, e.g., first light beam 14 and second light beam 16 are parallel to each other. In other embodiments, in which other devices than a plane-parallel plate, e.g., two separate laser diodes, are used to generate the two light beams 14, 16, the first and second light beams 14, 16 and the third and fourth light beams 24, 26 may be arranged in parallel planes, but at an angle with respect to each other.

In other embodiments, first and second light beams 14, 16 need not be arranged in parallel planes and may extend in an arbitrary manner, e.g., from the same source or from different sources, as long as they are focused in first focus 32 and second focus 34, respectively. For example, light source 13 may be configured to emit first light beam 14 from its location towards first focus 32 in a first direction, and to emit second light beam 16 from the same location towards second focus 34 in a second direction that is different from the first direction. Preferably, first and second light beams 14, 16 are emitted simultaneously. Of course, the above description also applies to third and fourth light beams 24, 26.

Although frame 18 has been described above as being substantially square, it should be understood that, in other embodiments, other frame geometries or cross-sections could be used, e.g., a circular frame, a frame having more than four corners, and the like, as long as two light beams that cross each other have a common focus in the interior of the frame. Further, in other embodiments, the emitter units and the detection units need not be arranged within a hollow frame, but may instead be arranged on the outer surface of a corresponding frame.

As already mentioned, in other embodiments, other devices than plane-parallel plates could be used for doubling (splitting) of a light beam. Further, each emitter unit may contain a plurality of separate light sources, instead of only one light source, and if necessary a plurality of separate focusing units (lenses), etc. may be provided. Further, it should be understood that more than two beam pairs that are separated from each other along the spray direction could be used, independent of whether a plane-parallel plate or another device is used for the generation of the light beams. In this manner, if necessary, the accuracy and reliability of the measurement can be increased.

For example, frame 18 could be made of metal such as steel or aluminum, preferably black anodized aluminum, and filters, e.g., narrow-band interference filters, could be used as windows in front of the respective detection units.

Adjacent to windows 15, 25, 52, 62 shown, e.g., in FIG. 1, appropriate deflection devices, e.g., deflection plates, may be arranged and serve to prevent the spray jet from impinging on the windows, thereby protecting the optical system of apparatus 10. If necessary, a slight positive pressure could be generated in the vicinity of the respective windows using a generated air stream (air curtain), such that the particles are prevented from hitting the respective windows.

Evaluation unit 70 may also be provided within frame 18 and output the measurement results, however, it may also be part of an external control device that only receives the detection signals of the detection units 50, 60. This may be achieved using both wired communication and wireless communication. Further, the evaluation unit may further have a very short access time of, e.g., two microseconds, such that all calculations can be performed very rapidly and a high temporal resolution is obtained accordingly.

Depending on design requirements, exemplary embodiments of the evaluation unit 70 of the present disclosure may be implemented in hardware and/or in software. The evaluation unit 70 can be configured using a digital storage medium, for example one or more of a ROM, a PROM, an EPROM, an EEPROM, a flash memory, etc., on which electronically readable control signals (program code—instructions) are stored, which interact or can interact with one or more programmable hardware components to execute programmed functions.

The (each) programmable hardware component can be formed by a processor, a computer processor (CPU=central processing unit), an application-specific integrated circuit (ASIC), an integrated circuit (IC), a computer, a system-on-a-chip (SOC), a programmable logic element, and/or a field programmable gate array (FGPA). A microprocessor is a typical component of a microcontroller according to the present teachings.

The digital storage medium can therefore be machine- or computer-readable. Some exemplary embodiments thus comprise a data carrier or non-transient computer readable medium which includes electronically readable control signals which are capable of interacting with a programmable computer system or a programmable hardware component such that one of the methods or functions described herein is performed. An exemplary embodiment is thus a data carrier (or a digital storage medium or a non-transient computer-readable medium) on which the program for performing one of the methods described herein is recorded.

In general, exemplary embodiments of the present disclosure, in particular the evaluation unit 70, are implemented as a program, firmware, computer program, or computer program product including a program, or as data, wherein the program code or the data is operative to perform one of the methods when the program runs on (is executed by) a processor or a programmable hardware component. The program code or the data can for example also be stored on a machine-readable carrier or data carrier, such as any of the types of digital storage media described above. The program code or the data can be, among other things, source code, machine code, bytecode or another intermediate code.

A program according to an exemplary embodiment can implement one of the methods or function during its performance, for example, such that the program reads storage locations and/or writes one or more data elements into these storage locations, wherein switching operations or other operations are induced in transistor structures, in amplifier structures, or in other electrical, electronic, optical, magnetic components, or components based on another functional or physical principle. Correspondingly, data, values, sensor values, or other program information can be captured, determined, or measured by reading a storage location. By reading one or more storage locations, a program can therefore capture, determine or measure sizes, values, variables, and other information, as well as cause, induce, or perform an action by writing in one or more storage locations, as well as control other apparatuses, machines, and components, and thus for example also perform any complex process that the evaluation unit according to the present teachings may be designed to perform.

Although some aspects of the present teachings have been described in the context of a device or apparatus, it is to be understood that these aspects also represent a description of a corresponding method, so that a block or a component of a device or apparatus is also understood as a corresponding method step or as a feature of a method step. In an analogous manner, aspects which have been described in the context of or as a method step also represent a description of a corresponding block or detail or feature of a corresponding device.

It is explicitly stated that all features disclosed in the description and/or the claims are intended to be disclosed separately and independently from each other for the purpose of original disclosure as well as for the purpose of restricting the claimed invention independent of the composition of the features in the embodiments and/or the claims. It is explicitly stated that all value ranges or indications of groups of entities disclose every possible intermediate value or intermediate entity for the purpose of original disclosure as well as for the purpose of restricting the claimed invention, in particular as limits of value ranges.

I claim:

1. An apparatus for determining a size of particles in a spray jet, comprising:
    a first emitter unit configured to emit a first light beam and a second light beam,
    a second emitter unit configured to emit a third light beam and a fourth light beam,
    a first focusing unit configured to focus the first and second light beams in a first focus and a second focus, respectively, the first focus being spaced apart from the second focus by a distance in a first direction (z),
    a second focusing unit configured to focus the third and fourth light beams in the first focus and the second focus, respectively,
    a first detection unit configured to detect an intensity of the first light beam and an intensity of the second light beam after passage through the first focus and the second focus, respectively,
    a second detection unit configured to detect an intensity of the third light beam and an intensity of the fourth light beam after passage through the first focus and the second focus, respectively, and
    an evaluation unit configured to determine the size of a particle that has passed through the first focus and the second focus based, at least in part, on the intensities detected by the first detection unit and the second detection unit.

2. The apparatus of claim 1, wherein:
    the first emitter unit is configured to emit the first light beam and the second light beam in parallel in a second direction and spaced apart in the first direction (z), the second direction (x) being perpendicular to the first direction (z), and
    the second emitter unit is configured to emit the third light beam and the fourth light beam in parallel in a third direction (y) and spaced apart in the first direction (z), the third direction (y) extending at an angle to the second direction (x).

3. The apparatus of claim 1, wherein the evaluation unit is configured to determine that the particle has passed through the first focus and the second focus by comparing the intensities of the first and second light beams detected by the first detection unit to the intensities of the third and fourth light beams detected by the second detection unit.

4. The apparatus of claim 3, wherein the evaluation unit is configured to:
    determine that a particle has passed through the first focus by determining that the detected intensities of the first and third light beams are below a predetermined threshold and/or differ by less than a predetermined amount, and
    determine that the particle has moved through the second focus by determining that the detected intensities of the second and fourth light beams are below the predetermined threshold and/or differ by less than the predetermined amount.

5. The apparatus of claim 4, wherein the evaluation unit is configured to determine a velocity of the particle based on a time difference between detections of minimum intensities of the first and second light beams and/or the third and fourth light beams and the distance between the first focus and the second focus.

6. The apparatus of claim 5, wherein the evaluation unit is configured to determine the size of the particle based on the determined velocity and averaging of durations of decreases of the intensities of the first and/or the second light beam detected by the first detection unit and/or decreases of the intensities of the third and/or the fourth light beam detected by the second detection unit.

7. The apparatus of claim 6, further comprising:
    a frame that is positionable with respect to the spray jet such that the spray jet passes through an interior of the frame, wherein the first emitter unit and the first detection unit, and the second emitter unit and the second detection unit, are respectively arranged at opposite positions of the frame, each of the first focus and the second focus being located at the center of the frame, and the first emitter unit and the first detection unit, and the second emitter unit and the second detection unit, are disposed within the frame and are protected from the outside by windows provided in the frame.

8. The apparatus of claim 6, wherein:

the first emitter unit and the second emitter unit each include a light source and a plane-parallel plate, the first and second light beams and the third and fourth light beams are each generated by reflection of a light beam emitted from the light source by the plane-parallel plate, and the first detection unit and the second detection unit each include a detection element comprising a photodiode and an optical system comprising a lens configured to focus the light beams onto the detection element.

9. The apparatus of claim 1, wherein the evaluation unit is configured to:

determine that the particle has passed through the first focus by determining that the detected intensities of the first and third light beams are below a predetermined threshold and/or differ by less than a predetermined amount, and determine that the particle has moved through the second focus by determining that the detected intensities of the second and fourth light beams are below the predetermined threshold and/or differ by less than the predetermined amount.

10. The apparatus of claim 1, wherein the evaluation unit is configured to determine a velocity of the particle that has passed through the first focus and the second focus based on the intensities of the first and/or the second light beam detected by the first detection unit and the intensities of the third and/or fourth light beam detected by the second detection unit.

11. The apparatus of claim 10, wherein the evaluation unit is configured to determine the velocity of the particle based on a time difference between detections of minimum intensities of the first and second light beams and/or the third and fourth light beams and the distance between the first focus and the second focus.

12. The apparatus of claim 10, wherein the evaluation unit is configured to determine the size of the particle based on the velocity and the duration of a decrease of the intensities of the first and/or the second light beam detected by the first detection unit and/or a decrease of the intensities of the third and/or the fourth light beam detected by the second detection unit.

13. The apparatus of claim 12, wherein the evaluation unit is configured to determine the size of the particle based on averaging durations of decreases of two or more of the detected intensities.

14. The apparatus of claim 1, further comprising:

a frame that is positionable with respect to the spray jet such that the spray jet passes through an interior of the frame, wherein the first emitter unit and the first detection unit, and the second emitter unit and the second detection unit are respectively arranged at opposite positions of the frame, each of the first focus and the second focus being located at the center of the frame.

15. The apparatus of claim 14, wherein the first emitter unit and the first detection unit, and the second emitter unit and the second detection unit, are disposed within the frame and are protected from the outside by windows provided in the frame.

16. The apparatus of claim 1, wherein the first emitter unit and the second emitter unit each include a light source and a plane-parallel plate, wherein the first and second light beams and the third and fourth light beams are each generated by reflection of a light beam emitted from the light source by the plane-parallel plate.

17. The apparatus of claim 1, wherein the first detection unit and the second detection unit each include a detection element and an optical system configured to focus the light beams onto the detection element.

18. An apparatus for determining a size of particles in a spray jet that is moving along a first direction (z), comprising:

one or more first light sources emitting a first light beam and a second light beam in parallel, one or more second light sources emitting a third light beam and a fourth light beam in parallel, one or more first lenses focusing the first light beam in a first focus and focusing the second light beam in a second focus, the first focus being spaced apart from the second focus in the first direction (z), one or more second lenses focusing the third light beam in the first focus and focusing the fourth light beam in the second focus, at least one first photodetector that detects an intensity of the first light beam and an intensity of the second light beam after the first light beam and the second light beam have passed through the first focus and the second focus, respectively, at least one second photodetector that detects an intensity of the third light beam and an intensity of the fourth light beam after the third light beam and the fourth light beam have passed through the first focus and the second focus, respectively, a processor, and a non-transitory computer readable medium comprising computer readable instructions that, when executed by the processor, cause the processor to determine the size of a particle that has passed through the first focus and the second focus based, at least in part, on the intensities detected by the at least one first photodetector and the at least one second photodetector.

19. The apparatus of claim 18, wherein the non-transitory computer readable medium comprises computer readable instructions that, when executed by the processor, cause the processor to determine that the particle has passed through the first focus and the second focus by comparing the intensities of the first and second light beams detected by the at least one first photodetector to the intensities of the third and fourth light beams detected by the at least one second photodetector.

20. A method for determining a size of particles in a spray jet, comprising:

emitting a first light beam and a second light beam, emitting a third light beam and a fourth light beam, focusing the first and second light beams in a first focus and a second focus, respectively, the first focus being spaced apart from the second focus by a distance in a first direction, focusing the third and fourth light beams in the first focus and the second focus, respectively, detecting an intensity of the first light beam and an intensity of the second light beam after passage through the first and the second focus, detecting an intensity of the third light beam and an intensity of the fourth light beam after passage through the first and the second focus, and determining the size of a particle that has passed through the first focus and the second focus based, at least in part, on the detected intensities.

\* \* \* \* \*